US00PP11570P

United States Patent [19]

Engelke

[11] Patent Number: Plant 11,570

[45] Date of Patent: Oct. 17, 2000

[54] ZOYSIAGRASS PLANT NAMED 'CROWNE'

[75] Inventor: Milton Charles Engelke, Parker, Tex.

[73] Assignee: The Texas A&M University System, College Station, Tex.

[21] Appl. No.: 09/076,973

[22] Filed: May 13, 1998

[51] Int. Cl.[7] ..... A01H 5/00

[52] U.S. Cl. ..... Plt./390

[58] Field of Search ..... Plt./390, 388

[56] References Cited

U.S. PATENT DOCUMENTS

P.P. 8,553 1/1994 Staton ..... Plt./390

OTHER PUBLICATIONS

R.H. White, M.C. Engelke and S.J. Morton, Performance of Zoysiagrass Cultivars and Elite DALZ Lines Under Linear Gradient Irrigation, TX Turfgrass Res.—1990, Consolidated Prog. Rep. PR–4748: 33–36.

M.C. Engelke, R.H. White, S.J. Morton and K.B. Marcum, Root Development in Selected Varieties of Each of Four Warm–season Turfgrass Genera, TX Turfgrass Res.—1991, Consolidated Prog. Rep. PR–4884: 10–17.

S.J. Morton, M.C. Engelke, R.H. White and K.B. Marcum, 1991 Update on Performance of Zoysiagrass Cultivars and Elite DALZ Lines Under Linear Gradient Irrigation. TX Turfgrass Res.—1991, Consolidated Prog. Rep. PR–4890: 36–42.

S.J. Morton, M.C. Engelke and R.H. White, Performance of Four Warm–season Turfgrass Genera Cultured in Dense Shade iii. Zoysia spp., TX Turfgrass Res.—1991, Consolidated Prog. Rep. PR–4894: 51–52.

USDA–NTEP. 1991 National Zoysiagrass Test–1991. U.S. Dept. Agric. Beltsville, MD. 1995 Prog. Rept., NTEP No. 96–6: 54 pp.

USDA–NTEP. 1991 National Zoysiagrass Test–1991, U.S. Dept. Agric. Beltsville, MD. Final Report 1992–95, NTEP No. 96–15:101 pp.

USDA–NTEP. 1991. National Zoysiagrass Test–1991, U.S. Dept. Agric. Beltsville, MD 1993 Pro. Rept., NTEP No. 94–5: 54 pp.

USDA–NTEP. 1991. National Zoysiagrass Test–1991, U.S. Dept. Agric. Beltsville, MD 1994 Prog. Rpt. NTEP No. 95–8: 66 pp.

K.B. Marcum and M.C. Engelke, Root Development of Zoysiagrasses Included in the 1991 National Turfgrass Evaluation Program Trial. TX Turfgrass Res.—1992, Consolidated Prog. Rep. PR–4978: 2–4.

S.J. Morton, M.C. Engelke, R.H. White and K.B. Marcum, Summarization of Zoysiagrass Performance Under Linear Gradient Irrigation, TX Turfgrass Res.—1992, Consolidated Prog. Rep. PR–4989: 38–44.

S.J. Morton and M.C. Engelke, Performance of Three Warm–Season Turfgrass Genera Cultured in Shade iii. TX Turfgrass Res.—1994. Consolidated Prog. Rep. PR–5139: 102–104.

S.J. Morton and M.C. Engelke. 1993. Zoysiagrass Entries in the 1991 National Turfgrass Evaluation Program Trial at Dallas. TX Turfgrass Res.—1994, Consolidated Prog. Rep. PR–5110: 18–21.

K.B. Marcum, M.C. Engelke, S.J. Morton and C. Dayton, Salinity Tolerances of Selected Bermudagrass and Zoysiagrass Genotypes. TX Turfgrass Res.—1994, Consolidated Prog. Rep. PR–5140: 105–107.

S.J. Morton and M.C. Engelke, Update to the 1991 National Turfgrass Evaluation Program (NTEP) Zoysiagrass Trial at TAES–Dallas. TX Turfgrass Res.—1994, Consolidated Prog. Rep. PR–5239: 10–12.

S.J. Morton, M.C. Engelke and K.G. Porter, Performance of Three Warm–Season Turfgrass Genera Cultured in Shade iii. Zoysia spp. TX Turfgrass Res.—1994, Consolidated Prog. Rep. PR–5242: 27–29.

S.K. Riffell, M.C. Engelke and S.J. Morton, 1995 Update to the 1991 National Turfgrass Evaluation Program (NTEP) Zoysiagrass Trial at TAES–Dallas. TX Turfgrass Res.—1995. Consolidated Prog. Rep. TURF –95–5: 26–33.

S.K. Riffell, M.C. Engelke and S.J. Morton, Performance of Three Warm–Season Turfgrasses Cultured in Shade: Zoysiagrass. TX Turfgrass Res.—1995. Consolidated Prog. Rep. TURF–95–11: 60–65.

I. Yamamoto and M.C. Engelke, Establishment of Warm–Season Turfgrasses by Three Vegetative Propagation Methods. TX Turfgrass Res.—1996. Consolidated Prog. Rep. TURF –96–4: 22–28.

I. Yamamoto and M.C. Engelke, 1996 Update of Zoysiagrass Performance under 90% Shade Conditions. TX Turfgrass Res.—1996. Consolidated Prog. Rep. TURF–96–11: 65–72.

James A. Reinhart, M.C. Engelke and Sharon J. Morton, Zoysiagrass Resistance To The Zoysiagrass Mite, Eriophyes Zoysiae (Acari: Eriophyidae), 1993, Inter. Turfgrass Soc. Res. J. 7: 349–352

R.H. White, M.C. Engelke, S.J. Morton and B.A. Ruemmele, Irrigation Water Requirement of Zoysiagrass, 1993 Inter. Turfgrass Soc. Res. J. 7: 587–593.

S.K. Braman, A.F. Pendley, R.N. Carrow and M.C. Engelke, Potential Resistence In Zoysiagrasses To Tawny Mole Crickets (Orthoptera: Gryllotalpid), 1994, Fl. Entomol. 77(3): 301–305.

J.A. Reinert, M.C. Engelke, J. C. Read, S.J. Maranz and B.R. Wiseman, Susceptibility Of Cool And Warm Season Turfgrasses To Fall Armyworm, *Spodoptera Frugiperda*, 1997, In R. M. Martin, et al. (eds.) Int. Turfgrass Soc. Res. J. 8: 1003–1011.

Y.L. Qian and M.C. Engelke, Evaluation of Zoysiagrass Genotypes for Shade Tolerance. TX Turfgrass Res.—1997. Consolidated Prog. Rep. TURF 97–24: 11p.

Y.L. Qian and M.C. Engelke, National Turfgrass Evaluation Program, (NTEP) Zoysiagrass Trial at TAES–Dallas, 1996 Consolidated Prog. Rep. TURF 97–29: 5p.

M.H. Hall, R.H. White, J.E. Gaudreau, W.G. Menn and G.R. Taylor. Zoysiagrass Cultivar Study. Consolidated Prog. Rep. TURF–97–33: 6p. .

*Primary Examiner*—Howard J. Locker

*Assistant Examiner*—Wendy A. Baker

*Attorney, Agent, or Firm*—Fulbright & Jaworski L.L.P.

[57] ABSTRACT

An asexually reproduced variety of perennial *Zoysia japonica* with a unique combination of characters including white stigmas, anthers which are 5.0 RP ¾, and a distinct DNA fingerprint.

2 Drawing Sheets

BRIEF SUMMARY OF THE INVENTION

The present invention relates to a new and distinct asexually reproduced variety of perennial zoysiagrass (*Zoysia japonica*).

BACKGROUND OF THE INVENTION

This invention relates to a new and distinct perennial zoysiagrass cultivar identified as 'Crowne' zoysiagrass (herein referred to as 'Crowne'), that was tested asDALZ8512. 'Crowne', a *Zoysia japonica*, is a chance hybrid of the maternal close 'Z20' (unpatented), obtained from Beltsville, MD in 1981, with an unknown pollen source from a zoysiagrass germplasm field nursery at TAES—Dallas. 'Crowne' has been vegetatively propagated by stolons and rhizomes in Dallas, Tex., and is uniform in growth expression through successive generations.

For purposes of registration under the "International Convention for the Protection of New Varieties of Plants" (generally known by its French acronym as the UPOV Convention) and noting Section 1612 of the Manual of Plant Examination Procedures, the new variety of zoysiagrass of the present invention is named 'Crowne'.

BRIEF DESCRIPTION OF THE DRAWINGS

FIG. 1 is a photograph of the leaf blade and ligule of 'Crowne'.

DETAILED DESCRIPTION OF THE PLANT

Figure 2:
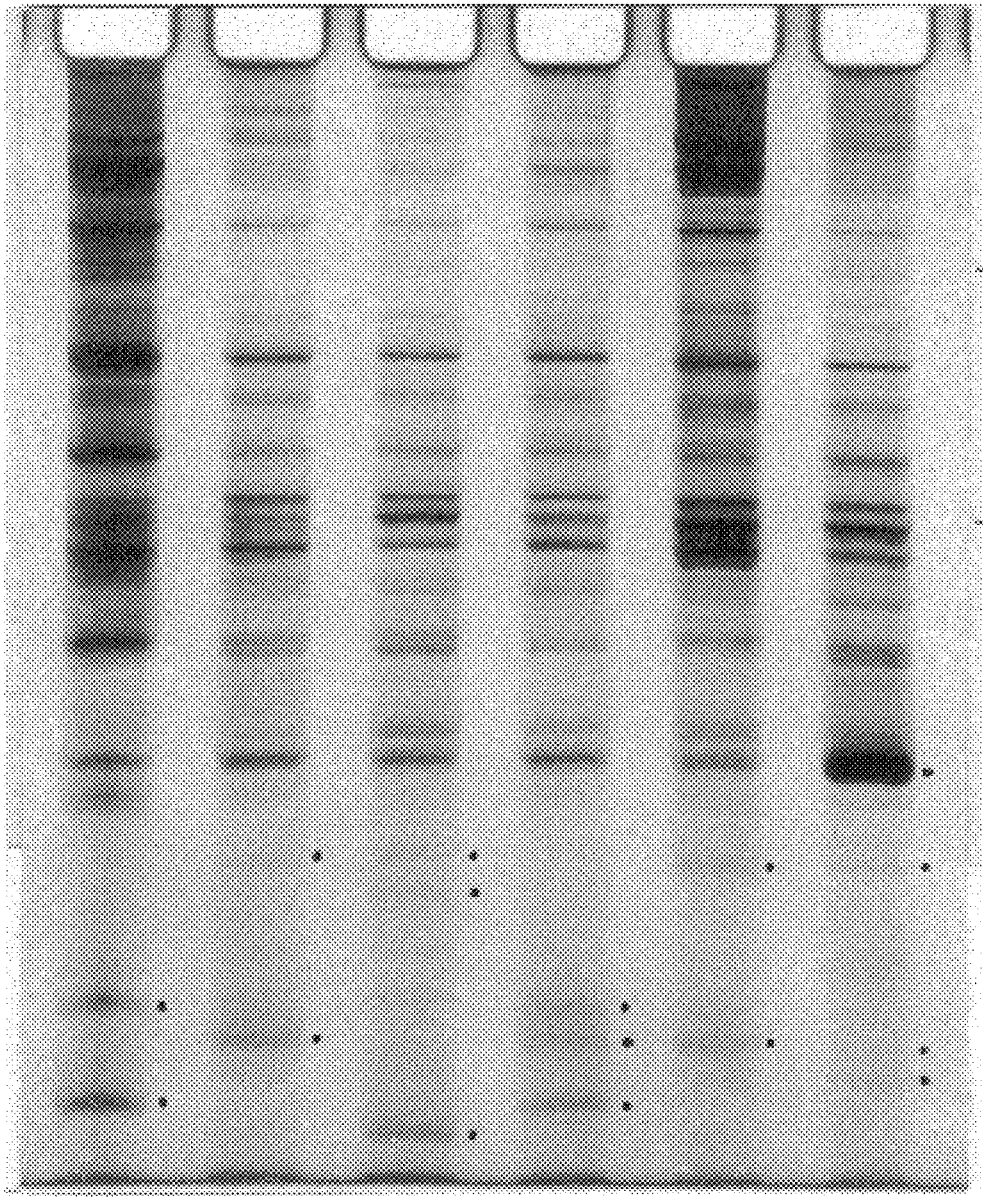
FIG. 2 is a DNA fingerprint of 'Crowne' in contrast to 'Meyer' (unpatented) zoysiagrass.

'Crowne' was characterized in greenhouse and field conditions. 'Crowne' is a unique variety of zoysiagrass developed as described above. 'Crowne' was identified as being unique and desirable and was then propagated by cutting of stolons and rhizomes, rooting them in soil, and planting of the rooted material to provide planting stock for studying performance and for comparison of morphological characters after propagation. 'Crowne' has been propagated by sod, plugs, sprigs, stolons and rhizomes in greenhouse and field studies by hand and mechanical propagation in Dallas, Tex. All distinguishing and defining characteristics are reliably reproduced in stable and firmly fixed form by such means through succeeding generations. Seed reproduction with self-fertility is not common in the Zoysia sp. No seedling establishment from 'Crowne' has been noticed in either greenhouse or field studies.

'Crowne' spreads by stolons and rhizomes. It has an intermediate to rapid establishment rate and has low water use requirements. When sprig (stolons) or plug plantings are made in early May, the area should achieve 50–60% average in Dallas, Tex. in 90–120 days, with complete coverage in 190–210 days, in comparison to 'Meyer' zoysiagrass which will require 360–400 days for full coverage. The stolons of 'Crowne' have a mean internode length of 17.7 mm between the second and third nodes, with a mean internode width of 0.9 mm and node diameter of 1.1; internode length between the fourth to fifth internode was 12.0 mm with a stolon width of 1.8 mm (Tables 1,2). This creates a proportionally short-thick internode unique to 'Crowne'. The stolons of 'Crowne' root adventitiously at the nodes. Color notations of plant tissues were based on the Munsell *Color Charts for Plant Tissues*, Munsell Color, Baltimore, Md., 1977. Light quality, photoperiod, and general growth of the plants affect color notations. The internode stolon color of 'Crowne' stolons exposed to full sun is 10R 3/2.

Leaf blades of 'Crowne' are rolled in the bud and are flat and stiff. The leaf blade length of 'Crowne' is from 72.7 to 126.6 mm and 2.96 to 3.23 mm in width (Tables 3,4). The leaf sheath of 'Crowne' is distinct from 'Meyer' (Table 5). The hairs on the abaxial leaf surface of 'Crowne' are sparse in number and are approximately 0.9 mm long. Measured under greenhouse conditions in January 1996, the genetic, adaxial leaf color of 'Crowne' is 2.5G 4/4 with 'El Toro' (U.S. Plant Pat. No. 5,845) having a leaf color of 2.5GY 5/2, and 'Meyer' having a color of 2.5G 3/4. The ligule of 'Crowne' is a fringe of silky hairs, approximately 2.5 mm in length for the longest hairs.

Thatch development is a function of age of stand, types of soils and other environmental and cultural conditions. Thatch development was determined in 3 year old field plantings comparing eight commercially available cultivars. 'Emerald', 'Miyako' (U.S. Plant Pat. No. 10,187) and 'Zeon' (unpatented) produced the greatest depth of thatch (26.3 mm); 'Crowne', 'Palisades' and 'De Anza' produced an intermediate amount of thatch (25, 23 and 23 mm, respectively), and 'Cavalier' (U.S. Plant Pat. No. 10,778) and 'Meyer' produced the least amount of thatch (20 and 19 mm, respectively).

'Crowne' has 5.0 RP 3/4 colored anthers and white colored stigmas, undistinguished in shade of color. The inflorescence of 'Crowne' is a terminal spike-like raceme, with spikelets on short pedicels. 'Crowne' has a mean length floral region of 23.1 mm with a mean of 25.3 florets per raceme.

The chromosome number of 'Crowne' is 40.

When 'Crowne' was compared with 59 other zoysiagrasses for salinity tolerance, it ranked number 33 in performance and was superior to 'Meyer' (Table 6). When compared to other commercial varieties for root growth, 'Crowne' was not different from 'El Toro' or 'Meyer' in average root depth, root weight, or clipping weights (Table 7).

'Crowne' was entered in the National Turfgrass Evaluation Program (NTEP). 'Crowne' in the National Turfgrass Evaluation Program Zoysiagrass Trial for the years 1992, 1993, and 1994 had mean quality ratings of 5.8, 5.8, and 5.5 for overall quality (Table 8).

'Crowne' shows intermediate resistance to the zoysiagrass mite (Table 9). The varieties 'Meyer', 'Belair' (unpatented), and most experimental zoysiagrasses are very susceptible to the mite. This mite has been found in Maryland, Texas, Florida, and all extensive zones of use for zoysiagrasses.

'Crowne' is distinguished from other zoysiagrass by its coarse texture, thick stolons, and intermediate to good stolon and rhizome production. It has moderate to good shade tolerance and low water use needs and is highly competitive under natural environmental conditions typical of north central Texas. 'Crowne' is intermediate to superior in its average growth rate and has good to excellent winter hardiness and will persist in regions north to Kansas, Missouri and Illinois.

TABLE 1

Internode length as measured between the second and third nodes, internode diameter of the third internode, and node diameter of the third node measured on zoysiagrass plants. Plants were growing in a growth chamber with a 14-hr daylength, March 1995.

| Genotype | Internode length mm | Internode diameter mm | Node diameter mm |
|---|---|---|---|
| 'Crowne' | 17.7 a* | 0.9 abc | 1.1 bc |
| 'Cavalier' | 18.4 a | 1.4 abc | 1.4 abc |
| 'Meyer' | 24.1 a | 2.0 a | 2.0 a |
| 'Palisades' (United | 29.9 a | 1.0 a | 1.7 ab |

TABLE 1-continued

Internode length as measured between the second and third nodes, internode diameter of the third internode, and node diameter of the third node measured on zoysiagrass plants. Plants were growing in a growth chamber with a 14-hr daylength, March 1995.

| Genotype | Internode length mm | Internode diameter mm | Node diameter mm |
|---|---|---|---|
| States Plant Patent Application Serial Number 09/078,184) | | | |
| 'El Toro' | 39.8 a | 1.4 abc | 1.4 abc- |

*Analysis of variance by General Linear Models, with means followed by the same letter not significantly different using Tukey's Studentized Range (HSD), alpha = 0.05. Only selected means presented.

TABLE 2

Zoysiagrass internode lengths and stolon width measurements from the fourth to the fifth nodes taken February 1988 on greenhouse grown plants.

| Genotype | Internode length mm | Stolon width mm |
|---|---|---|
| 'Emerald' (unpatented) | 6.2 e* | 1.0 ghi |
| 'Crowne' | 12.0 b–e | 1.8 a |
| 'Palisades' | 12.3 b–e | 1.6 b |
| 'Meyer' | 16.5 bc | 1.5 b |
| 'Cavalier' | 16.7 bc | 1.1 efg |

*Means followed by the same letter are not significantly different using the Waller-Duncan k ratio test (k ratio = 100). Only selected means presented.

TABLE 3

Leaf blade width and length measured on the third youngest leaf of zoysiagrass. Plants were growing in a growth chamber with a 14-hr daylength, March 1995.

| Genotype | Blade width mm | Blade length mm |
|---|---|---|
| 'Cavalier' | 1.3 d* | 60.7 cd |
| 'Meyer' | 2.6 c | 74.3 bc |
| 'Crowne' | 3.0 abc | 72.7 bc |
| 'El Toro' | 3.3 abc | 68.3 bcd |
| 'Palisades' | 3.4 ab | 75.6 bc |

*Analysis of variance by General Linear Models, with means followed by the same letter not significantly different using Tukey's Studentized Range (HSD), alpha = 0.05. Only selected means presented.

TABLE 4

Zoysiagrass leaf measurements taken February 1988 on the fourth youngest leaf from greenhouse grown plants.

| Genotype | Blade width mm | Blade length mm |
|---|---|---|
| 'Cavalier' | 1.8 ij* | 58.9 e |
| 'Emerald' | 2.0 fgh | 30.6 f |
| 'Crowne' | 3.2 b | 126.6 b |
| 'Palisades' | 3.4 b | 101.1 c |
| 'Meyer' | 3.3 b | 82.3 d |

*Means followed by the same letter are not significantly different using the Waller-Duncan k ratio test (k ratio = 100). Only selected means presented.

TABLE 5

Zoysiagrass leaf sheath length measurements taken February 1988 on the fourth youngest leaf from greenhouse grown plants.

| Genotype | Sheath length mm |
|---|---|
| 'Emerald' | 16.3 ij |
| 'Cavalier' | 28.9 ef |
| 'Meyer' | 30.7 cd |
| 'Crowne' | 42.9 b* |
| 'Palisades' | 51.25 a |

*Means followed by the same letter are not significantly different using the Waller-Duncan k ratio test (k ratio = 100). Only selected means presented.

TABLE 6*

Average percent shoot salt injury (average of 20 rating dates) on zoysiagrass entries in the 1991 NTEP† Trials.

| Entry | Source | Species‡ | % Injury |
|---|---|---|---|
| 'Diamond' (U.S. Plant Patent No. 10,636) | NTEP 20 | matrella | 33 ab£ |
| 'El Toro' | NTEP 13 | japonica | 38 a–e |
| 'Emerald' | NTEP 10 | jap x tenu | 42 a–h |
| 'Cavalier' | NTEP 17 | matrella | 42 a–h |
| 'Crowne' | NTEP | japonica | 46 e–k |
| 'Palisades' | NTEP | japonica | 46 e–k |
| 'Belair' | NTEP 11 | japonica | 50 f–k |
| 'Meyer' | NTEP 09 | japonica | 58 lmn |
| 'Korean Common' (unpatented) | NTEP 07^ | japonica | 76 pq |

*Selected data set; complete data set includes 59 varieties and cultivars.
†NTEP = National Turfgrass Evaluation Program.
‡Species identity.
£Means followed by the same letter are not significantly different, based on the Waller-Duncan k-ratio t-test (k-ratio = 100)

In Marcum, K. B., M. C. Engelke, S. J. Morton and C. Dayton. 1994. Salinity tolerances of selected bermudagrass and zoysiagrass genotypes. TX Turfgrass Res.—1993, Consolidated Prog. Rep. PR 5140: 105–107.

TABLE 7

Average mean root depth of zoysiagrass grown in flexible tubes in greenhouse studies, Dallas, TX.

| Variety | Average Mean Root Depth mm | Total Root Weight mm | Clippinge Weights mm |
|---|---|---|---|
| 'Cavalier' | 255 | 278 | 243 |
| 'Belair' | 296 | 330 | 286 |
| 'Palisades' | 318 | 457 | 452 |
| 'Emerald' | 330 | 461 | 241 |
| 'Meyer' | 333 | 411 | 466 |
| 'Crowne' | 355 | 497 | 406 |
| 'El Toro' | 356 | 473 | 391 |
| MSD | 79 | 161 | 267 |

*MSD = minimum significant difference for comparison of means within columns based on the Waller-Duncan k-ratio test where k = 100.

In Marcum, K.B., M.C. Engelke, S.J. Morton, and R.H. White. 1995. Rooting characteristics and associated drought resistance of zoysiagrasses. Agron.

J. 87:534–538.

TABLE 8

Mean Turfgrass quality ratings of vegetative zoysiagrass cultivars grown in the National Turfgrass Evaluation Program at 23 locations in the US for 1992, 1993, 1994, and 1995.

| Variety | 1992 mm | 1993 mm | 1994 | 1995 | Overall 4-Yr Avg. mm |
|---|---|---|---|---|---|
| 'Cavalier' | 6.0 | 6.2 | 5.9 | 6.0 | 5.9 |
| TC 2033 | 5.8 | 6.1 | 6.1 | 6.0 | 5.9 |
| 'Sunburst' (unpatented) | 5.8 | 5.9 | 5.8 | 5.9 | 5.8 |
| TC 5018 | 5.8 | 5.8 | 5.9 | 5.7 | 5.8 |
| 'Emerald' | 5.7 | 6.2 | 6.0 | 5.7 | 5.8 |
| 'Omni' (unpatented) | 5.6 | 6.1 | 6.1 | 6.0 | 5.7 |
| QT 2004 | 5.6 | 6.0 | 5.9 | 5.6 | 5.6 |
| DALZ8508 | 5.6 | 6.1 | 5.7 | 5.6 | 5.6 |
| 'Palisades' | 5.8 | 5.8 | 5.5 | 5.4 | 5.6 |
| DALZ9006 | 5.6 | 6.0 | 5.6 | 5.5 | 5.6 |
| 'Crowne' | 5.8 | 5.8 | 5.5 | 5.4 | 5.6 |
| 'El Toro' | 5.8 | 5.6 | 5.3 | 5.4 | 5.5 |
| CD 259-13 | 5.3 | 5.5 | 5.7 | 5.5 | 5.4 |
| 'Meyer' | 5.3 | 5.7 | 5.8 | 5.5 | 5.4 |
| QT 2047 | 5.4 | 5.4 | 5.3 | 5.2 | 5.3 |
| 'Belair' | 5.0 | 5.6 | 5.6 | 5.0 | 5.2 |
| DALZ8516 | 4.7 | 5.4 | 5.0 | 5.0 | 4.9 |
| 'Diamond' | 4.4 | 5.0 | 4.6 | 4.4 | 4.4 |
| DALZ8501 | 4.9 | 4.3 | 4.0 | 4.0 | 4.3 |
| DALZ8701 | 4.2 | 4.1 | 3.7 | 3.6 | 3.8 |
| LSD VALUE | 0.2 | 0.2 | 0.2 | 0.2 | 0.2 |

To determine statistical differences among entries, subtract one entry's mean from another entry's mean. Statistical difference occurs when this value is larger than the corresponding LSD value (LSD 0.05).

In National Zoysiagrass Test—1991. Final Report 1992–95, NTEP No. 96-15; (Table 4); United States Department of Agriculture, Agricultural Research Service, Beltsville Agricultural Research Center, Beltsville, Md. 20705.

TABLE 9

Mean number of mite-damaged leaves per zoysiagrass plant (n = 18).

| Cultivar | Leaf Texture Class | 3April92 | 24April92 | Combined Dates |
|---|---|---|---|---|
| DALZ9006 | 31 | 0.2a* | 0.2 a | 0.2 a |
| DALZ8508 | 2 | 0.7 b | 0.6 ab | 0.6 b |
| DALZ8516 | 2 | 1.8 d | 0.3 ab | 1.0 b |

TABLE 9-continued

Mean number of mite-damaged leaves per zoysiagrass plant (n = 18).

| Cultivar | Leaf Texture Class | 3April92 | 24April92 | Combined Dates |
|---|---|---|---|---|
| 'Emerald' | 3 | 1.3 bc | 0.9 b | 1.1 b |
| DALZ8501 | 1 | 1.4 cd | 2.6 c | 2.0 c |
| 'Crowne' | 4 | 5.4 ef | 2.3 c | 3.9 d |
| 'El Toro' | 4 | 5.6 ef | 2.8 c | 4.2 d |
| TC2033 | 2 | 4.4 e | 4.3 d | 4.4 d |
| 'Palisades' | 4 | 7.5 fg | 4.0 cd | 5.8 e |
| CD2031 | 2 | 7.6 gh | 7.9 e | 7.8 f |
| 'Diamond' | 1 | 7.8 gh | 9.4 ef | 8.6 g |
| DALZ8701 | 1 | 9.3 h | 9.4 ef | 9.4 g |
| 'Cavalier' | 3 | 9.1 h | 9.8 ef | 9.5 g |
| 'Meyer' | 2 | 9.9 h | 9.9 ef | 9.9 g |
| 'Belair' | 2 | 10.0 h | 9.9 f | 9.9 g |
| JZ-1 | 4 | 10.0 h | 9.9 f | 10.0 g |

*Data transformed using log (X + 0.5) for analysis. Means in a column followed by the same letter are not significantly different by Waller-Duncan k-ratio test (k = 100) (P = 0.05).
1 Textural class of zoysiagrass where 1 = short, narrow leaves; 2 = short, wide leaves; 3 = long, narrow leave; and 4 = long, wide leaves.

Reinert, J.A., M.C. Engelke, and S.J. Morton. 1993. Zoysiagrass resistance to the zoysiagrass mite, *Eriphyes zoysiae* (Acari: Eriophyidae). In R.N. Carrow, N.E. Christians, and R.C. Sherman (Eds.). International Turfgrass Society Research Journal 7. Intertec Publishing Corp., Overland Park, Kans. pp. 349–352.

DETAILED SUMMARY OF DNA FINGERPRINT ANALYSIS

Drs. Bassam and Caetano-Anolles of the University of Tennessee performed the DNA analysis. The zoysiagrass amplification profiles were obtained using primer of sequence 5'-GCCCGCCC-3', and are compared to the standard 'Meyer'. Complex banding patterns and amplification fragment length polymorphism's were obtained in all cases. Results indicate bands fall into two categories, those that are common to the species, and those that in combination are characteristic of the cultivar (some identified by dots).

I claim:

1. A new and distinct cultivar of *Zoysia japonica* plant as herein shown and described.

* * * * *

MEYER | DALZ8501 | DIAMOND | CAVALIER | CROWNE | DALZ8701